(12) United States Patent
Zahn

(10) Patent No.: US 7,981,323 B2
(45) Date of Patent: Jul. 19, 2011

(54) SELENIUM CONTAINING ELECTRICALLY CONDUCTIVE COPOLYMERS

(75) Inventor: Steffen Zahn, Pennsburg, PA (US)

(73) Assignee: Konarka Technologies, Inc., Lowell, MA (US)

(*) Notice: Subject to any disclaimer, the term of this patent is extended or adjusted under 35 U.S.C. 154(b) by 413 days.

(21) Appl. No.: 11/777,386

(22) Filed: Jul. 13, 2007

(65) Prior Publication Data

US 2009/0014693 A1  Jan. 15, 2009

(51) Int. Cl.
*H01B 1/12* (2006.01)
(52) U.S. Cl. .............. 252/500; 549/50; 562/899
(58) Field of Classification Search .............. 252/500; 549/50; 562/899; 528/377
See application file for complete search history.

(56) References Cited

U.S. PATENT DOCUMENTS

| | | | |
|---|---|---|---|
| 4,732,901 A | 3/1988 | Buckle | |
| 5,300,575 A | 4/1994 | Jonas et al. | |
| 6,585,914 B2 | 7/2003 | Marks et al. | |
| 6,645,401 B2 | 11/2003 | Giles et al. | |
| 6,676,857 B2 | 1/2004 | Heeney et al. | |
| 6,695,978 B2 | 2/2004 | Worrall et al. | |
| 6,709,808 B2 | 3/2004 | Lelental et al. | |
| 7,071,289 B2 | 7/2006 | Sotzing | |
| 7,125,479 B2 | 10/2006 | Sotzing | |
| 7,700,008 B2 * | 4/2010 | Hsu et al. | 252/519.33 |
| 7,722,785 B2 * | 5/2010 | Hsu et al. | 252/500 |
| 2004/0010115 A1 | 1/2004 | Sotzingt | |

(Continued)

FOREIGN PATENT DOCUMENTS

EP  1 318 163 A1  6/2003

(Continued)

OTHER PUBLICATIONS

Novak "Structure, stability and aromaticity of bis-heteropentalenes", THEOCHEM (1997), 398-399, 315-323 (Abstract only).*

(Continued)

*Primary Examiner* — Mark Kopec
(74) *Attorney, Agent, or Firm* — Fish & Richardson P.C.

(57) ABSTRACT

Monomeric, oligomeric and polymeric electrically conductive compounds and methods of making the compounds having a repeating unit having formula P1, as follows:

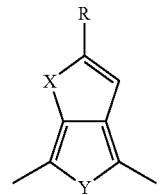

where X is S or Se, Y is S or Se, wherein one or both of X and Y is Se, R is a substituent group capable of bonding to the ring structure. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid, phosphoric acid, carboxylic acid, halo, amino, nitro, hydroxyl, cyano or epoxy moieties. Electrical devices utilizing the electrically conductive polymers is also disclosed.

14 Claims, 1 Drawing Sheet

U.S. PATENT DOCUMENTS

| | | | |
|---|---|---|---|
| 2006/0074250 A1 | 4/2006 | Zahn et al. | |
| 2006/0076557 A1 | 4/2006 | Waller | |
| 2007/0085061 A1* | 4/2007 | Elder et al. | 252/500 |
| 2007/0170401 A1* | 7/2007 | Hsu et al. | 252/500 |
| 2007/0278453 A1* | 12/2007 | Zahn et al. | 252/500 |
| 2007/0278458 A1* | 12/2007 | Martello et al. | 252/519.21 |
| 2008/0023676 A1* | 1/2008 | Hsu | 252/512 |
| 2009/0140219 A1 | 6/2009 | Zahn | |
| 2009/0278093 A1* | 11/2009 | Heeney et al. | 252/500 |

FOREIGN PATENT DOCUMENTS

| | | |
|---|---|---|
| EP | 1 652 850 | 5/2006 |
| EP | 1 728 810 | 12/2006 |
| EP | 1 754 736 A1 | 2/2007 |
| EP | 2 014 664 | 1/2009 |
| EP | 2 014 665 | 1/2009 |
| JP | 2005-035955 | 2/2010 |
| KR | 2003-0047749 A | 6/2003 |

OTHER PUBLICATIONS

Jones et al "The Vilsmeir reaction of fully conjugated carbocycles and heterocycles", Organic Reactions (Hoboken, NJ) (1997), 49, no pages given (Abstract Only).*

Guliev et al "Quantum-chemical calculations of spectroscopic parameters of heteroaromatic sulfur and seleniumcompounds", Izvestiya Akademii Nauk SSSR, Seriya Khimicheskaya (1986), (10), 2251-3 (Abstract Only).*

Abronin et al "Quantum chemical analysis of selenium-77 chemical shifts in condensed selenophenes", Chem Scripta (1982), 19(2), 75-7 (Abstract Only).*

H Atom Adducts—New Free Radicals?, J. Am. Chem. Soc. 85, 484 (1963).

John A. Walker, et al, New Chemically Prepared Conducting "Pyrrole Blacks", J. Polym. Sci. Part A Polym. Chem., vol. 26, pp. 1285-1294 (1988).

Irina P. Beletskaya, et al, The Heck Reaction As a Sharpening Stone of Palladium Catalysis, Chem. Rev. 2000, 100, pp. 3009-3066.

Keith Fagnou, et al, Rhodium-Catalyzed Carbon-Carbon Bond Forming Reactions of Organometallic Compounds, Chem. Rev. 2003, 103, pp. 169-196.

Norio Miyaura, et al, Palladium-Catalyzed Cross-Coupling Reactions of Organoboron Compounds, Chem. Rev. 1995, 95, pp. 2457-2483.

Ei-Ichi Negishi, et al, Palladium-Catalyzed Alkynylation, Chem. Rev. 2003, 103, pp. 1979-2017.

Jwanro Hassan, et al, Aryl-Aryl Bond Formation One Century After The Discovery of The Ullmann Reaction, Chem. Rev. 2002, 102, pp. 1359-1469.

Gronowitz, S.; "New Synthesis of 3-Bromo-Thiophene and 3, 4-Dibromo-Thiophene"; Acta Chem. Scand.; vol. 13, No. 5; 1959; pp. 1045-1046; XP002594517.

John, J.A., et al; "Synthesis of Polyphenylene Derivatives by Thermolysis of Enediynes and a Dialkynylaromateic Monomers", Tetrahedron, Elsevier Science Publishers; vol. 53, No. 45; Nov. 10, 1997; pp. 15515-15534; XP004106381.

Ketcham R.; Synthesis of Tetrathiafulvalene Doubly Fused to the 3, 4-Position of Selenophene, J. Org. Chem.; vol. 49; pp. 1117-1119; 1984.

Konar A. et al, "Selenopheno[3,4-b]Selenophene—The Third "Classical" Selenophrene"; Tetrahedron; vol. 36, No; pp. 3317-3323; 1980.

Kulik, W. et al; "Dimetalation of Isopropenylacetylene Application in the Synthesis of 3-Methylselenophen, 3-Methylene-2,3-Dihydroselenophen and the Tellurlum Analogues", Tetrahedron Letters; vol. 24, No. 21; 1983; pp. 2203-2204; XP002580630.

Litvinov, V.P., et al; "Selenopheno[,3-c]Thiophene—A Third Isomeric Selenophenothiophene", Russian Chemcial Bulletin; vol. 20, No. 7, 1971; p. 1498; XP002580629.

Yasuike S., et al; "Syntheses of Novel Dithieno[2,3-,3', 2'-f]- and Kethieno[3,4-b', 4'-f] Heteroepins Containing Group 14, 15 and 16 Heavier Elements"; Heterocycles, Vo. 45, No. 10; Oct. 1, 1997; pp. 189-1902; XP001539729.

Yasuike S., et all; "Syntheses of Novel Group 15 and 16 Thieno[2,3-b], Thieno[3,4-b-, and Thieno[3-2-b] Heteroles"; Heterocycles, vol. 48, No. 10; 1997; pp. 1891-1894.

Yavuz, M.S. et al; "Optically Transparent Conducting Polymers from Fused Heterocycles"; Material Research Society Proceeding; vol. 965.

Ye, X-S, et al.; "Synthetic Applications of 3, 4-Bis9Trimethylsilyl) Thiophene; Unsymmetrically 3, 4-Disubstituted Thiophenese and 3, 4-Didehydrothiophene"; J. Org. Chem. vol. 62; 1997; pp. 1940-1954; XP002594518.

* cited by examiner

SELENIUM CONTAINING ELECTRICALLY CONDUCTIVE COPOLYMERS

CROSS-REFERENCE TO RELATED APPLICATIONS

The subject matter of the instant application also is related to U.S. patent application Ser. No. 11/777,362, filed on Jul. 13, 2007 and application Ser. No. 12/353,462, filed on even date herewith, and both of which are entitled "HETEROCYCLIC FUSED SELENOPHENE MONOMERS"; the disclosure of which is hereby incorporated by reference.

BACKGROUND OF THE INVENTION

The present invention is directed to compositions of matter, including, without limitation, electrically conductive polymers comprising polymerized heterocyclic fused ring monomers, methods of producing such compositions of matter, and to applications utilizing such compositions of matter.

Polymers formed from thiophene and substituted thiophene monomers, which possess relatively low band gaps (Eg), demonstrate measurable electrical conductivity. Such polymers are often referred to as intrinsically conducting polymers. The term, band gap (Eg), refers to the energy difference between electronic energy levels called the conduction band and the valence band. The band gap exhibited by a given polymer depends upon a variety of factors including the structure of the monomer making up the polymer. For example, polythiophene demonstrates a band gap of 2.1 eV, poly(2-decylthieno[3,4-b]thiophene) demonstrates a band gap of 0.92 eV and poly(2-phenylthieno[3,4-b]thiophene) demonstrates a band gap of 0.85 eV.

Conducting polymers having only aromatic repeating units in the polymer backbone are typically not soluble in water. Consequently, such polymers are typically processed using organic solvents. Several methods have been employed to increase the solubility of intrinsically conducting polymers in various organic solvents. Such methods include (1) forming a derivative of the monomer to increase the solubility of the side chains of the monomer in a given organic solvent; (2) modifying the polymer backbone by employing oligomeric conjugated systems and flexible spacers; and (3) using charge compensating dopants.

U.S. Pat. No. 5,300,575 (the '575 patent), which is herein incorporated by reference in its entirety, discloses dispersions of polythiophenes which are suitable for use as antistatic coatings for plastic moldings. These polythiophenes are prepared by polymerizing the corresponding monomer in the presence of oxidizing agents typically used for the oxidative polymerization of pyrrole and/or with oxygen or air in the presence of a polyanion. The polythiophenes of the '575 patent have a relatively low Eg of 1.7 eV compared to poly (thiophene) which has an Eg of 2.1 eV.

The polythiophenes of the '575 patent are prepared by polymerizing 3,4-ethylenedioxythiophene in the presence of poly(styrene sulfonic acid). The resulting linear polymer is purified using both anion and cation exchange resins wherein poly(styrene sulfonate) serves as a charge compensating dopant. The resulting polymer forms a colloidal dispersion in water because poly(styrene sulfonate) is soluble in water and demonstrates a strong ionic interaction with the cationic polymeric backbone.

What is needed are intrinsically conducting polymers which exhibit useful bandgaps for industrial applications, which can be readily dispersed in water and which are stable in solution to afford a useful shelf life.

BRIEF SUMMARY OF THE INVENTION

The invention relates to novel mono-, oligo- and polymeric compounds comprising fused heterocyclic groups. The invention further relates to their use as semiconductors or charge transport materials, in optical, electro-optical or electronic devices. The invention further relates to optical, electro-optical or electronic devices comprising the novel compounds.

The present invention includes compositions of matter formed from polymerized units of heterocyclic fused ring monomer units. In one embodiment of the present invention, the invention provides monomeric, oligomeric and polymeric compositions having repeating unit having formula P1, as follows:

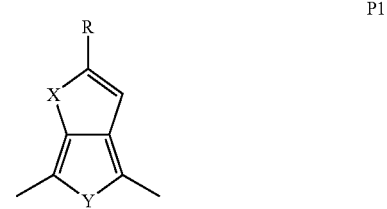

P1 where X is S or Se, Y is S or Se, wherein one or both of X and Y is Se, R is a substituent group. R may be any substituent group capable of bonding to the ring structure of P1. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F. R' and R" are independently of each other H, aryl or alkyl with 1 to 12 C-atoms The polymer may include end-groups independently selected from functional or non-functional end-groups. The repeating structures according to the present invention may be substantially identical, forming a homopolymer, or may be copolymeric nature by selecting monomers suitable for copolymerization. The repeating unit may be terminated in any suitable manner known in the art and may include functional or non-functional end groups. In addition, dispersions and solutions containing P1 and polymeric acid doped compositions of P1. In one embodiment, the composition includes an aqueous dispersion of a polymeric acid doped polymer according to P1.

A copolymer according to the present invention may include a monomeric, oligomeric and copolymeric compounds having a repeating unit having formula having a repeating unit having formula C1, as follows:

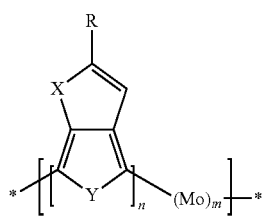

C1 wherein X, Y and R are defined as above in formula P1, n and m are independently selected integers having a total n+m of greater than or equal to 2, and in some cases greater than 4. End groups are independently selected from functional or non-functional end-groups. In one embodiment n may equal 1. R is the same as the groups defined for formula P1. The n-unit substructure and m-unit substructure of the copolymer may be arranged in any fashion making up the copolymer including, but not limited to random copolymers, graft copolymers, block copolymers, and dendritic structures. Mo in the formula C1 structure may be any electroactive or non-electroactive monomer copolymerizable with the n-unit substructure of formula C1 including, but not limited to thieno[3,4-b]thiophenes, and substituted thiophenes.

One polymer consists of poly(selenolo[2,3-c]thiophene). The polymers of this invention may include copolymers further comprising polymerized units of an electroactive monomer. Electroactive monomers may be selected from the group consisting of thiophenes, thieno[3,4-b]thiophene, thieno[3,2-b]thiophene, substituted thiophenes, substituted thieno[3,4-b]thiophenes, substituted thieno[3,2-b]thiophene, dithieno[3,4-b:3',4'-d]thiophene, selenophenes, substituted selenophenes, pyrrole, bithiophene, substituted pyrroles, phenylene, substituted phenylenes, naphthalene, substituted naphthalenes, biphenyl and terphenyl, substituted terphenyl, phenylene vinylene, substituted phenylene vinylene, fluorene, substituted fluorenes. In addition to electroactive monomers, the copolymers according to the present invention may include polymerized units of a non-electroactive monomers.

The polymers of the present invention may include polymerized units of selenolo[2,3-c]thiophene and may further comprise an oligomer comprising selenolo[2,3-c]thiophene which is end group functionalized, polymerized units of 3,4-ethylenedioxythiophene and polymerized units of pyrrole.

The polymers of this invention can be doped with conventional p-dopants or n-dopants to modify the electrical properties of such polymers.

The electrically conductive polymer of this invention and compositions formed therefrom can be used for any purpose for which conductive polymers are useful. For example, the compositions of matter according to this invention can be utilized in a variety of industrial applications including electrochromic and electroluminescent displays, electrolytic capacitors, optically transparent or non-transparent electrodes, conductive polymer housings for EMI Shielding of sensitive electronic equipment such as microprocessors, infrared, radio frequency and microwave absorbing shields, flexible electrical conducting connectors, conductive bearings, brushes and semiconducting photoconductors junctions, electrodes, optically transparent or non-transparent corrosion-preventing coatings for corrodible materials such as steel, antistatic materials and optically transparent or non-transparent coatings for packaging or protecting electronic components, carpet fibers, waxes for floors in computer rooms, antistatic finishes for displays, coatings for windows for automobile, aircraft, and building solar energy control, electrostatic dissipative packaging and handling of containers for electronics and the like.

Another embodiment of the invention relates to polythiophenes and polyselenophenes formed from monomeric or oligomeric structural units formula M1, as follows:

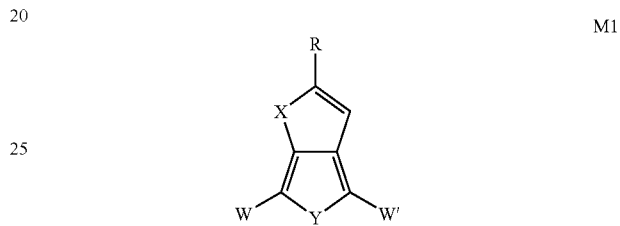

M1 where X is S or Se, Y is S or Se, wherein one or both of X and Y is Se, R is a substituent group. R may be any substituent group capable of bonding to the ring structure of P1. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH═CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F. R' and R" are independently of each other H, aryl or alkyl with 1 to 12 C-atoms. W and W' are H, halogen atoms, e.g., F, Cl, Br, and I, metallorganics, e.g., MgCl, MgBr, MgI, $Sn(R_2)_3$, where $R_2$ is $C_{1-6}$ alkyl or $C_{1-6}$ alkyl ether, boronic acid, boronic ester, vinyl units, e.g., —CH═CHR$_3$ where R$_3$ is H or $C_{1-6}$ alkyl, ether, i.e., —OC$_{1-6}$ alkyl, esters, i.e., —COOC$_{1-6}$ alkyl, —S—COR$_4$ and —COR$_4$ where R$_4$ is H or $C_{1-6}$ alkyl, —C≡CH, and polymerizable aromatic rings such as phenyl, naphthalene, pyrrole, and thiophene.

Another embodiment of the present invention includes a process for preparing electrically conductive polymers and copolymers. The polymerization reaction of the monomers described above may take place through one of several reaction mechanisms. Reactions suitable for use with the present invention include 1) aqueous phase/oxidant polymerization, 2) organic solvent phase/oxidant polymerization, 3) aqueous phase/organic phase/oxidant polymerization, 4) metal catalyst polymerization, 5) electrochemical polymerization and 6) solid state polymerization.

An embodiment of the present invention includes polymerized units of selenolo[2,3-c]thiophene comprising the steps of reacting selenolo[2,3-c]thiophene in the presence of water, a polyanion and an oxidant under reactions conditions sufficient to form the polymer comprising polymerized units of selenolo[2,3-c]thiophene. Polyanions for use in the aqueous phase reaction may be selected from the group consisting of polyacrylic acid, polymethacrylic acid, polyphosphonic acid, polyphosphoric acid, fluorinated sulfonic acid polymers, such as NAFION®, polymaleic acid, polystyrene sulfonic acid and polyvinyl sulfonic acid. The acids used may vary in molecular weight to afford different physical and electronic properties. Furthermore, the sulfonation level of the sulfonic acids may also vary widely to again tailor physical as well as electronic properties of the dispersions. Oxidants for use in the aqueous phase and the organic phase reaction may be selected from the group consisting of $Fe_2(SO_4)_3$, $FeCl_3$, $Fe(ClO_4)_3$, $H_2O_2$, $K_2Cr_2O_7$, sodium persulfate, potassium persulfate, ammonium persulfate, potassium permanganate, copper tetrafluoroborate, iodine, air and oxygen.

An advantage of the polymer compositions of the present invention is that, in one embodiment of the invention, the composition may be easily prepared, readily storable and reduce or eliminate environmental problems associated with use of dispersions formed from organic solvents. For example, water-borne dispersions of the compositions of matter of this invention can be cast by conventional methods to provide uniform, thin films that possess utility in numerous applications including electrochromic displays, optically transparent electrodes and antistatic coatings.

Another advantage of the present invention is that the polymerization reactions take place with desirable alignment of the monomer components during the polymerization reaction, providing for intrinsically conducting polymers having desirable electrical properties, including useful bandgaps.

Still another advantage of the present invention is that the polymers of the present invention may be formed into a variety of products including, but not limited to, hole injection materials, charge transport materials, semiconductors, and/or conductors, in optical, electrooptical or electronic devices, polymeric light emitting diodes (i.e., PLED), electroluminescent devices, organic field effect transistors (i.e., FET or OFET), flat panel display applications (e.g., LCD's), radio frequency identification (i.e., RFID) tags, printed electronics, ultracapacitors, organic photovoltaics (i.e., OPV), sensors, lasers, small molecule or polymer based memory devices, electrolytic capacitors or as hydrogen storage materials.

Other features and advantages of the present invention will be apparent from the following more detailed description of certain embodiments, taken in conjunction with the accompanying drawings which illustrate, by way of example, the principles of the invention.

DETAILED DESCRIPTION OF THE INVENTION

Figure 1:
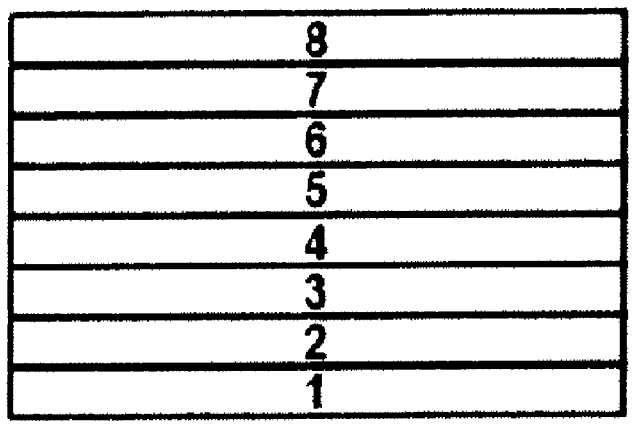
FIG. 1 is a schematic of a light emitting device including one or more layers comprising the inventive polymer.

This invention includes compositions of matter that comprise intrinsically conducting polymers including polymerized units of fused heterocyclic ring structure monomers. Polymer, as defined herein, shall mean a composition of matter having polymerized units of heterocyclic fused monomer structure repeating units. The polymers according to embodiments of the invention may be linear, branched or crosslinked polymeric structures. These compositions of matter can be prepared to exhibit a variety of properties desired for numerous end-use applications.

More particularly, such compositions of matter include monomeric, oligomeric, polymeric and copolymeric compounds having a repeating unit having formula P1, as follows:

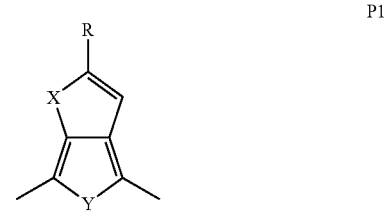

P1 where X is S or Se, Y is S or Se, wherein one or both of X and Y is Se, R is a substituent group. R may be any substituent group capable of bonding to the ring structure of P1. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH═CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F. R' and R" are independently of each other H, aryl or alkyl with 1 to 12 C-atoms. In addition, dispersions and solutions containing P1 and polymeric acid doped compositions of P1. In one embodiment, the composition includes an aqueous dispersion of a polymeric acid doped polymer according to P1.

Selenolo[2,3-c]thiophene-2,5-diyl and selenolo[2,3-c]thiophene, as utilized herein, shall mean the following structure:

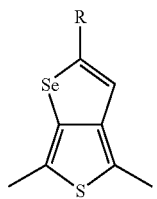

Selenolo[3,4-b]thiophene-2,5-diyl and selenolo[3,4-b]thiophene, as utilized herein, shall mean the following structure:

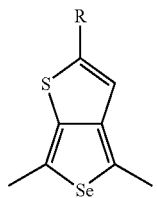

Selenolo[2,3-b]selenophene-2,5-diyl and selenolo[2,3-b]selenophene, as utilized herein, shall mean the following structure:

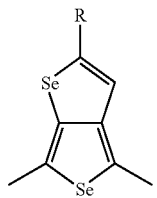

Copolymer, as defined herein, shall mean a composition of matter having polymerized units of heterocyclic fused monomer structure repeating units and polymerized monomers different than the heterocyclic fused monomer structure. The compositions of the present invention are not limited to the homopolymeric structures above and may include hetereopolymeric or copolymeric structures. The copolymeric structures may be any combination of alternating copolymers (e.g., alternating A and B units), periodic copolymers (e.g., (A-B-A-B-B-A-A-A-A-B-B-B)$_n$), random copolymers (e.g., random sequences of monomer A and B), statistical copolymers (e.g., polymer sequence obeying statistical rules) and/or block copolymers (e.g., two or more homopolymer subunits linked by covalent bonds). The copolymers may be branched or linked, provided the resultant copolymer maintains the properties of electrical conductivity.

The term, substrate, as defined herein, shall mean a solid material (which may be flexible or rigid) suitable for deposition of the compositions of matter according to this invention. Substrates can be formed of materials including, but not limited to glass, organic polymers, plastic, silicon, minerals, semiconducting materials, ceramics, metals, oxides, alloys and the like. The substrate may be electrically conductive or insulative.

The term, electroactive monomer, as defined herein, shall mean a monomer which is capable of polymerization or copolymerization resulting in a polymer having electrically conductive properties such as electrical conductivity, semiconductivity, electroluminescence, electrochromicity or photovoltaic properties.

The term, non-electroactive monomer, as defined herein, shall mean a monomer which is capable of polymerization or copolymerization which does not exhibit the properties set forth under the definition of electroactive monomer.

The term, band gap, as defined herein, shall mean the energy difference between electronic energy levels called the conduction band and the valence band.

The term, substituted, as defined herein, as used with respect to a composition of matter, shall mean an electron-rich or electron deficient group appended to such composition of matter. Useful substituents include, but are not limited to, H, hydroxyl, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbonyl.

The term, heteroaryl, as defined herein, shall mean a compound having the ring structure characteristic ring compounds, such as, but not limited to pyridine, pyrrole, thiophene, imidazole, or other similar ring structures. The heteroaryl group, while a substituent can itself have additional substituents (e.g. the substituents disclosed under this definition).

The term, aryl, as defined herein, shall mean a compound having the ring structure characteristic of benzene, naphthalene, phenanthrene, anthracene, etc. (e.g., the 6-carbon ring of benzene or the condensed 6-carbon rings of the other aromatic derivatives). For example, an aryl group may be phenyl (e.g., $C_6H_5$) or naphthyl (e.g., $C_{10}H_7$). The aryl group, while a substituent can itself have additional substituents (e.g. the substituents disclosed under this definition).

The term, alkyl, as defined herein, shall mean a paraffinic hydrocarbon group which may be derived from an alkane by dropping one hydrogen from the formula. Examples are methyl ($CH_3$—), ethyl $C_2H_5$—), propyl ($CH_3CH_2CH_2$—), isopropyl (($CH_3$)$_2$CH—) and tert-butyl (($CH_3$)$_3$C—).

The term, halogen, as defined herein, shall mean one of the electronegative elements of group VIIA of the periodic table (fluorine, chlorine, bromine and iodine).

The term, perfluoroalkyl, as defined herein, shall mean an alkyl group in which every hydrogen atom is replaced by a fluorine atom.

The term, perfluoroaryl, as defined herein, shall mean an aryl group in which every hydrogen atom is replaced by a fluorine atom.

The term, sulfoxyl, as defined herein, shall mean a group of composition RS(O)— where R is an alkyl, aryl, cycloalkyl, perfluoroalkyl or perfluoroaryl group. Examples include, but are not limited to methylsulfoxyl, phenylsulfoxyl, and the like.

The term, sulfonyl, as defined herein, shall mean a group of composition RS(O)$_2$— where R is an alkyl, aryl, cycloalkyl, perfluoroalkyl, or perfluoroaryl group. Examples include, but are not limited to methylsulfonyl, phenylsulfonyl, p-toluenesulfonyl, and the like.

The term, acyl, as defined herein, shall mean an organic acid group in which the -hydroxyl of the carboxyl group is replaced by another substituent to form the structure R(C═O)—. Examples include, but are not limited to acetyl, benzoyl, and the like.

The term, alpha position, as defined herein, shall mean a bond, ring position, substitutent group or other polymer propagating location that permits polymerization by any known polymerization technique.

A monomer useful in one embodiment of the present invention includes selenolo[2,3-c]thiophene, which includes three alpha positions for forming a linearly propagating and/or branched polymers. Polymers according to this embodiment of the invention may be propagated from the selenolo[2,3-c]thiophene to form polymerized units by effecting reaction at the alpha positions (represented by an asterisk) of the monomer depicted in formula M2, as follows:

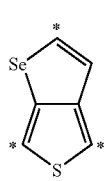

M2

The reactive alpha positions of the M2 monomer can react with additional M1 monomers to form a homopolymer of polymerized units or can react with one or more additional electroactive monomers or non-electroactive monomers to form copolymers, including random copolymers, graft copolymers, block copolymers, and dendritic structures.

The three alpha position structure shown and described above with respect to selenolo[2,3-c]thiophene monomers is equally applicable to selenolo[3,4-b]thiophene and selenolo[3,4-b]selenophene. In addition, the above structures may include substituent groups and/or copolymeric structures.

Electroactive monomers may be selected from the group consisting of thiophenes, thieno[3,4-b]thiophene, thieno[3,2-b]thiophene, substituted thiophenes, substituted thieno[3,4-b]thiophenes, substituted thieno[3,2-b]thiophene, dithieno[3,4-b:3',4'-d]thiophene, selenophenes, substituted selenophenes, pyrrole, bithiophene, substituted pyrroles, phenylene, substituted phenylenes, naphthalene, substituted naphthalenes, biphenyl and terphenyl, substituted terphenyl, phenylene vinylene, substituted phenylene vinylene, fluorene, substituted fluorenes. In addition to electroactive monomers, the copolymers according to the present invention may include polymerized units of a non-electroactive monomers.

One embodiment of the present invention includes a copolymer having a repeating unit having formula C1, as follows:

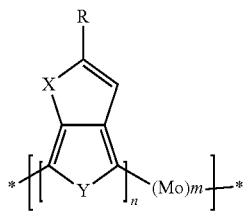

C1 wherein X, Y and R are defined as above in formula P1, n and m are independently selected integers having a total n+m of greater than or equal to 2, and in some cases greater than 4. End groups are independently selected from functional or non-functional end-groups. In one embodiment n may equal 1. R is the same as the groups defined for formula P1. The n-unit substructure and m-unit substructure of the copolymer may be arranged in any fashion making up the copolymer including, but not limited to random copolymers, graft copolymers, block copolymers, and dendritic structures. Mo in the formula C1 structure may be any electroactive or non-electroactive monomer copolymerizable with the n-unit substructure of formula C1 including, but not limited to selenolo[3,4-b]thiophenes, selenolo[2,3-c]thiophenes and selenolo[3,4-b]selenophene as well as any other heteroaryl or aryl.

Substituted thieno[3,4-b]thiophenes that may be utilized in Mo in formula C1, above, that may be incorporated into the polymers of the present invention to form a copolymer are represented by the formula:

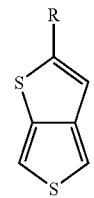

wherein R=$C_1$ to $C_{12}$ primary, secondary or tertiary alkyl group, phenyl, substituted phenyl, cyclohexyl, naphthalenic, hydroxyl, alkyl ether, carboxylic acid, carboxylic ester, perfluoroalkyl, perfluoroaryl, and a sulfonic acid.

Additional substituted thiophenes that may be utilized in Mo in formula C1, above, to be incorporated into the polymers of the present invention to form a copolymer are represented by the formula:

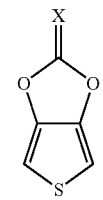

where X denotes S, O, Se, or NH.

Additional substituted thiophenes utilized in Mo in formula C1, above, to be incorporated into the polymers of the present invention to form a copolymer are represented by the formula:

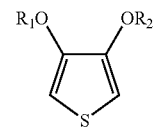

wherein $R_1$ and $R_2$ are independently selected from the group consisting of H, C1-C4 alkyl groups, 1,2 cyclohexylene radical, phenyl substituted phenyl and the like.

The compositions of matter according to this invention also contemplate oligomers comprising heterocyclic fused ring monomers which are endgroup functionalized and incorporated into either block copolymers or coupled with difunctional reactants known in the art (as an example hydroxyl endgroups could be coupled with diisocyanates or acid chlorides). Such oligomers provide a convenient method for controlling the conjugation length of the compositions of matter of this invention. The conjugation length in the oligomeric structure can be varied to achieve desired properties for a variety of applications.

The compositions of matter of the present invention may also include repeating units of non-electroactive monomers which are capable of being polymerized with selenolo[2,3-c] thiophene provided that the presence of such non-electroactive monomers does not adversely affect the electroactive properties of the resulting composition of matter.

The compositions of matter of this invention can be utilized as dispersions by forming or dissolving the desired polymer (including copolymers and oligomers) in water, a mixture of a water-miscible organic solvent or an organic solvent. Dispersions containing the compositions of matter according to this invention can be applied via conventional processes including ink jet printing, screen printing, roll to roll printing processes, spin coating, meniscus and dip coating, spray coating, brush coating, doctor blade application, curtain casting and the like. The amount of polymer (including copolymers and oligomers) to be incorporated into the solution or dispersion may vary depending upon a variety of factors including the molecular weight of the composition of matter and the end-use application. The actual amount of composition of matter to be introduced into the dispersion is readily determined without undue experimentation.

The dispersed films may be dried by conventional techniques including evaporation to remove the solvent to provide the desired film. Drying may be effected at room temperature or any temperature which does not adversely affect the properties of the resulting film. However, to obtain higher processing speeds, the film can be dried at elevated temperatures provided that such temperatures do not adversely affect the properties of the resulting film. However, depending on processing conditions and the specific polymer or oligomer higher temperatures may be desirable.

The compositions of matter of this invention can be utilized in a variety of conventional applications including antistatic coatings, electrically conductive coatings, electrochromic devices, photovoltaic devices, light emitting diodes, flat panel displays, photoimageable circuits, printable circuits, thin film transistor devices, batteries, electrical switches, capacitor coatings, corrosion resistant coatings, electromagnetic shielding, sensors, LED lighting and other optoelectronics. (Optoelectronics is a field of technology that combines the physics of light with electricity. Optoelectronics encompasses the study, design and manufacture of hardware devices that convert electrical signals into photon signals and vice versa. Any device that operates as an electrical-to-optical or optical-to-electrical transducer is considered an optoelectronic device.) The electrical conductivity of the compositions of matter according to the present invention can be readily modified, if necessary, to meet the requirements of any of the previously mentioned applications by doping these compositions of matter with conventional acidic dopants (p-dopants) and basic dopants (n-dopants) known in the art.

Suitable p-dopants include mineral acids such as HCl, $HNO_3$, $H_2SO_4$, $H_3PO_4$, HBr, HI; organic sulfonic acids such as dodecyl benzene sulfonic acid, lauryl sulfonic acid, camphor sulfonic acid, organic acid dyes, methane sulfonic acid, toluene sulfonic acid, polymeric sulfonic acids such as poly(styrene sulfonic acid) and copolymers; carboxylic acids such as acetic acid, propionic acid, butyric acid, hexanoic acid, adipic acid, azelaic acid, oxalic acid, and polymeric polycarboxylic acids such as poly(acrylic acid) poly(maleic acid), poly(methacrylic acid), phosphonic acids, phosphoric acids, fluorinated ion exchange polymers (e.g., Nafion®) and copolymers containing these acids. Conventional mixed dopants such as mineral acids/organic acids can also be utilized to impart desired electroactive character to the compositions of matter of this invention.

While p-doping is can be employed, the compositions of matter according to this invention can also be n-doped with conventional basic dopants including but not limited to Na, K, Li and Ca. Other suitable dopants include $I_2$, $(PF_6)^-$, $(SbF_6)^-$, and $FeCl_3$.

The compositions of matter of this invention are well suited for use in fabricating certain components of light emitting diodes (LEDs). LEDs typically possess numerous layers including a substrate, and indium tin oxide (ITO) anode, a hole injection layer, a hole transport layer, a light emitting layer, an electron transport layer, an electron injection layer and a cathode. The p-doped compositions of matter of this invention are particularly suited toward replacing the indium tin oxide anode of the LED. The p-doped compositions of matter of this invention are also particularly suited toward use as the hole injection layer of the LED. Undoped compositions of matter of this invention can be utilized in the hole transport layer, the light emitting layer and/or the electron transport layer of the LED. The p-doped compositions of matter of this invention are particularly suited toward replacing the indium tin oxide electrode in organic photovoltaic cells. The p-doped compositions of matter of this invention are also particularly suited toward use as the hole extraction layer n organic photovoltaic cells. Undoped compositions of matter of this invention can be utilized in the hole transport layer, the light absorbing layer and/or the electron transport layer in organic photovoltaic cells. The p-doped compositions of matter of this invention are particularly suited toward replacing the manganese oxide electrode in electrolytic capacitors.

Admixtures of the compositions of matter of this invention with other electroactive materials such as laser dyes, other electroactive polymers, hole transport or electron transport materials including electroactive organometallic compounds are also embodied in this invention.

The compositions of matter of this invention can also be utilized to prepare optically transparent conductive coatings for use in optically transparent electrodes, transparent conductive adhesives, stealth coatings, transparent EMF shielding, touch screens, flat screen displays, flat antennas for mobile applications, transparent capacitor plates, and the like. Additional applications for polymers according to the present invention may include, but are not limited to, hole injection materials, charge transport materials, semiconductors, and/or conductors, in optical, electrooptical or electronic devices, polymeric light emitting diodes (i.e., PLED), electroluminescent devices, organic field effect transistors (i.e., FET or OFET), flat panel display applications (e.g., LCD's), radio frequency identification (i.e., RFID) tags, printed electronics, ultracapacitors, organic photovoltaics (i.e., OPV), sensors, lasers, small molecule or polymer based memory devices, electrolytic capacitors or as hydrogen storage materials.

Photovoltaic devices have specific similarities to LEDs and are likewise capable of fabrication using the compositions of the present invention. Instead of electrical voltage placed across the device to produce light for the LED device, the input of light (e.g. sunlight) produces a voltage difference across the device to produce an electric current. The layers of the LED and photovoltaic devices are similar but not equivalent. Light harvesting organics or polymers comprise an intermediate layer with hole transport/electron transport layers optionally placed between the anode and cathode. The compositions of matter of this invention can be utilized as the anode and hole injection layers (doped) or in the light harvesting layers (undoped).

A photovoltaic cell includes an electrochemical device that converts electromagnetic radiation to electrical energy. While not wishing to be bound by theory, the conversion may be accomplished through a charge separation event that occurs after absorption of a photon, which causes the creation of an excited state, which may be referred to as an exciton. Typically the semiconductor domains, such as a p-type semiconductor in intimate contact with an n-type semiconductor, are sandwiched in one or more active layers between two electrodes, wherein at least one electrode is sufficiently transparent to allow for the passage of the photon.

The photovoltaic cells can comprise at least four components, two of which are electrodes. One component is a transparent first electrode such as an indium tin oxide layer on a plastic or glass substrate. This layer functions as a charge carrier, typically the anode. In addition, the anode allows ambient light to enter the device. Another component includes a second electrode typically fabricated from metal, such as calcium or aluminum. This metal may be coated onto a supporting surface such as a plastic or glass sheet. The second electrode also carries current. Between these electrodes are the third and fourth components including discrete layers or mixtures of p- and n-type semiconductors. The p-type material may be referred to as a light harvesting component or layer. The p-type material absorbs photons of a particular energy and generates a state in which an electron is promoted to an excited energy state. The promotion of the electron leaves a positive charge or "hole" in the ground state energy levels. As known in the art, this is known as exciton formation. The exciton migrates to a junction between p-type and n-type material, forming a charge separation or dissociation of the exciton. The electron and "hole" charges are conducted through the n-type and p-type materials respectively to the electrodes resulting in the flow of electric current out of the cell. The p-type semiconductor may include mixtures or blends of materials including the oligomeric, copolymer or polymeric materials according to an embodiment of the present invention, including but not limited to selenolo[3,4-b]thiophenes, selenolo[2,3-c]thiophenes and selenolo[3,4-b] selenophene containing oligomers, copolymers and polymers. The n-type component may include materials with a strong electron affinity including, for example, carbon fullerenes, titanium dioxide, cadmium selenium, and polymers and small molecules that are specifically designed to exhibit n-type behavior.

The aqueous dispersions described can be used as hole injection layers in organic light emitting diodes. These devices are most commonly best represented in a sandwich graphic as shown in FIG. 1. An organic light emitting device can contain a large amount of layers of various materials to obtain desired results. Most commonly, a device consists of a substrate (1), an anode (2), an hole injection layer (4), a light emitting polymer (6), and a cathode (8). Interlayers may be placed between the various layers as depicted in FIG. 1. In addition, the hole injection layer (3) may also function as anode (2) as well as hole injection layer (3) resulting in a more simplified device structure.

Figure 2:
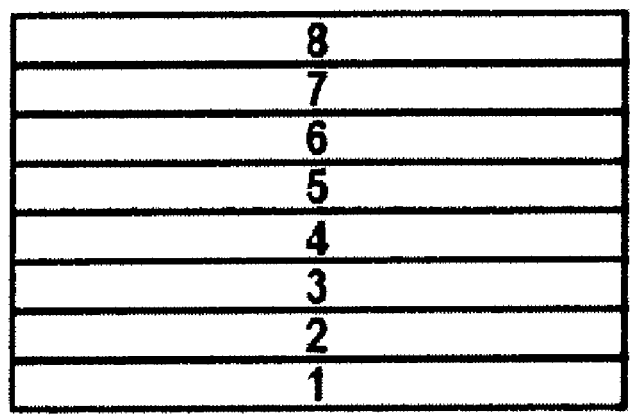
FIG. 2 is a schematic of a photovoltaic device including one or more layers comprising the inventive polymer.

The aqueous dispersions described can be also used as hole injection layers in photovoltaic devices. These devices are most commonly best represented in a sandwich graphic as shown in FIG. 2. A photovoltaic device can contain a large amount of layers of various materials to obtain desired results. Most commonly, a device consists of a substrate (1), an optional anode (2), optional interlayer(s) (3), a hole injection (hole extraction) layer (4), optional interlayers (5), active layer (mixture of electron donor and acceptor materials) (6), optional interlayers (7) and cathode (8). Interlayers may be placed between the various layers as depicted in FIG. 2.

The compositions of matter according to this invention can be utilized in fabricating electrochromic devices which permit or prevent the transmission of light through transparent substrates by application of a voltage across conventional substrates known in the art. Other uses for the compositions of matter according to the present invention include electromagnetic shielding and dimmable mirrors.

Doped compositions of matter according to this invention can be utilized as antistatic coatings applied from water-borne or organic solvent-borne solutions or dispersions to substrates enumerated under the definition section. Such antistatic coatings can include admixtures with other polymers including emulsions to achieve a balance of conductivity and film properties such as adhesion to the appropriate substrate. The compositions of matter of this invention can also be utilized as coatings or additives to various articles of commerce to render the article conductive including the various substrates noted above for antistatic coatings and electroplating processes, printable circuits, photoimageable circuits, semiconductor devices and the like.

The invention furthermore relates to photovoltaic devices which contain, the polymer built up from the structural units of the formula P1. Photovoltaic devices of this type may comprise the following structure:

1st layer:
An electrode comprising an oxide, such as indium tin oxide layer on a plastic or glass substrate.

2nd layer:
A conductive film formed from an aqueous dispersion containing a doped conducting polymer and a polyanion (i.e. PEDOT/PSS);

3rd and/or 4$^{th}$ layer:
Discrete layers or mixtures of p- and n-type semiconductors, wherein the p-type material includes monomeric, oligomer, copolymeric or polymer material having the following repeating structure P1:

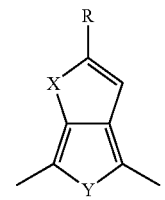

P1 where X is S or Se, Y is S or Se, wherein one or both of X and Y is Se, R is a substituent group. R may be any substituent group capable of bonding to the ring structure of P1. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F. R' and R" are independently of each other H, aryl or alkyl with 1 to 12 C-atoms; and, 4th layer:

A second electrode typically fabricated from metal, such as calcium or aluminum.

The invention furthermore relates to photovoltaic devices which contain, the polymer built up from the structural units of the formula P1. Photovoltaic devices of this type may comprise the following structure:

1st layer:

An electrode comprising an oxide, such as indium tin oxide layer on a plastic or glass substrate.

2nd layer:

A conductive film formed from an aqueous dispersion containing doped polymerized units of Selenolo[2,3-c]thiophene and fluorinated sulfonic acid polymer.

3rd and/or 4th layer:

Discrete layers or mixtures of p- and n-type semiconductors, wherein the p-type material includes monomeric, oligomer, copolymeric or polymer material having the following repeating structure P1:

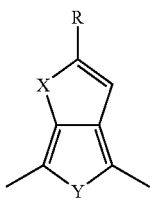

P1 where X is S or Se, Y is S or Se, wherein one or both of X and Y is Se, R is a substituent group. R may be any substituent group capable of bonding to the ring structure of P1. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties.

In certain embodiments R may include alpha reactive sites, wherein branched oligomeric, polymeric or copolymeric structures of the selenium containing ring structure may be formed. In certain embodiments, R may include R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F. R' and R" are independently of each other H, aryl or alkyl with 1 to 12 C-atoms; and, 4th layer:

A second electrode typically fabricated from metal, such as calcium or aluminum.

The invention furthermore relates to photovoltaic devices which contain, the polymer built up from the structural units of the formula P1. Photovoltaic devices of this type may comprise the following structure:

1st layer:

An electrode comprising an oxide, such as indium tin oxide layer on a plastic or glass substrate.

2nd layer:

A conductive film formed from an aqueous dispersion containing doped polymerized units of Selenolo[2,3-c]thiophene and fluorinated sulfonic acid polymer.

3rd and/or 4th layer:

Discrete mixtures of p- and n-type semiconductors, wherein the p-type material is a polythiophene and/or polyselenophene and the n-type semiconductor is a fullerene and/or a small molecule and/or oligomeric/polymeric n-type semiconductor.

4th layer:

A second electrode typically fabricated from metal, such as calcium or aluminum.

While certain embodiments of this invention involves use of the compositions of matter as transparent/conductive materials, conductive nontransparent coatings based on the compositions of matter of this invention have utility in specific applications where transparency is not important but electrical conductivity is important. Certain applications such as antistatic coatings may require pigmentation which will result in loss of transparency as well as various conductive paint applications. Printed circuits employing these materials will also generally not require transparency.

The invention relates to the use of certain polythiophenes and polyselenophenes (e.g., formula P1) as solid electrolyte in electrolyte capacitors, and to electrolyte capacitors which contain these polythiophenes and polyselenophenes as solid electrolytes. In particular, certain embodiment of the present invention include aqueous dispersions of oligomer, copolymers and polymers including, but not limited, to selenolo[3,4-b]thiophenes, selenolo[2,3-c]thiophenes and selenolo[2,3-c]selenophene containing materials having the formula P1.

The invention furthermore relates to electrolyte capacitors which contain, as solid electrolytes, the polymer built up from the structural units of the formula P1. Solid electrolyte capacitors of this type have the following structure:

1st layer:
Foil of an oxidizable metal, for example aluminum, niobium or tantalum;

2nd layer:
Oxide layer of the metal;

3rd layer:
electrically conductive monomeric, oligomer, copolymeric or polymer material having the following repeating structure P1:

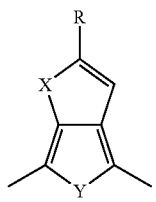

P1 where X is S or Se, Y is S or Se, wherein one or both of X and Y is Se, R is a substituent group. R may be any substituent group capable of bonding to the ring structure of P1. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH═CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluororaryl, carboxylic acids, esters and sulfonic acid groups, perfluoro, $SF_5$, or F. R' and R" are independently of each other H, aryl or alkyl with 1 to 12 C-atoms; and, if desired, 4th layer:
Contact, for example a thin layer of substances that are good conductors of the electrical current, such as conductive silver, copper or paint filled with carbon black.

While the above capacitor has been described with respect to polymer formula P1, copolymers may also be used. The present invention includes polythiophenes obtainable by oxidative polymerization of specific thiophenes that are particularly suitable as solid electrolytes for electrolyte capacitors. These specific polythiophenes can be applied adherently in a particularly simple manner, without impacting their conductivity, to the metal foils used as anodes in electrolyte capacitors, and give capacitors which are distinguished by good electrical properties, for example a high, substantially frequency-independent capacity, and furthermore by low dielectric losses and low leakage currents.

The polythiophenes and polyselenophenes to be used according to the invention may be produced directly on the side of a metal foil that is coated with an oxide coating and used as an anode. In some cases, these foils are made from aluminum, niobium or tantalum. The polythiophenes and polyselenophenes are produced by oxidative polymerization of monomers of the present invention, by applying a monomer, such as selenolo[2,3-c]thiophene-2,5-diyl, selenolo[3,4-b]thiophene-2,5-diyl, or selenolo[3,4-b]-selenophene-2,5-diyl containing compounds and the oxidants, if desired in the form of solutions, either separately one after the other or, if suitable, together onto the side of the metal foil that is coated with the oxide coating, and completing the oxidative polymerization, if appropriate, depending on the activity of the oxidant used, by warming the coating. Alternatively, a dispersion containing polymers according to the invention may be directly coated onto the metal oxide surfaces to form the conductive layer.

Additives such as dimethyl sulfoxide, ethylene glycol, diethylene glycol, mannitol, propylene 1,3-glycol, butane 1,4-glycol, N-methylpyrrolidone, sorbitol, glycerol, propylene carbonate and other appropriate high boiling organics may be added to dispersions of the compositions of matter of this invention to improve conductivity.

Additional additives include conductive fillers such as particulate copper, silver, nickel, aluminum, carbon black, carbon nanotubes and the like. Non-conductive fillers such as talc, mica, wollastonite, silica, clay, $TiO_2$, dyes, pigments and the like can also be added to the dispersions to promote specific properties such as increased modulus, surface hardness, surface color and the like.

Depending on the final application of the material, examples of additional water soluble or dispersible materials which can be added include, but are not limited to polymers, dyes, coating aids, carbon nanotubes, nanowires, surfactants (e.g., fluorosurfactants such as Zonyl® FSO series non-ionic fluorosurfactants (e.g., available commercially from DuPont) with structure $R_fCH_2CH_2O(CH_2CH_2O)_xH$, where $R_f$=F$(CF_2CF_2)_y$, x=0 to about 15 and y=1 to about 7, acetylenic diol based surfactants such as Dynol™ and Surfynol® series (e.g., available commercially from Air Products and Chemicals, Inc), organic and inorganic conductive inks and pastes, charge transport materials, crosslinking agents, and combinations thereof. The materials can be simple molecules or polymers. Examples of suitable other water soluble or dispersible polymers comprise at least one conductive polymer such as polythiophenes, polyanilines, polyamines, polypyrroles, polyacetylenes, and combinations thereof.

The dispersions of the compositions of matter of this invention may also comprise antioxidants, UV stabilizers and surfactants when required for specific applications. Surfactants are typically added to the dispersions to control stability, surface tension, and surface wettability. Surfactants may include acetylenic diols. Viscosity modifiers (such as associative thickeners) can also be added to such dispersions to adjust viscosity for specific end uses.

The compositions of matter according to the present invention can be prepared by a variety of methods. The compositions of matter according to the present invention can be prepared utilizing an aqueous phase polymerization method wherein selenolo[2,3-c]thiophene-2,5-diyl, selenolo[3,4-b]thiophene-2,5-diyl, or selenolo[3,4-b]-selenophene-2,5-diyl containing compounds, a polyanion and an oxidant are reacted in the presence of water under reaction conditions sufficient to form poly(selenolo[3,4-b]thiophene). In another embodiment, selenolo[2,3-c]thiophene, a polyanion and an oxidant are reacted in the presence of water under reaction conditions sufficient to form poly(selenolo[2,3-c]thiophene). The temperature for conducting the polymerization is not critical but may affect the rate of polymerization.

Another embodiment of the invention relates to the use of polythiophenes and polyselenophenes which are formed from structural units formula M1, as follows:

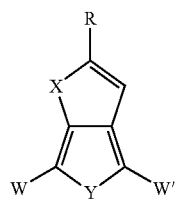

M1 where X is S or Se, Y is S or Se, wherein one or both of X and Y is Se, R is a substituent group. R may be any substituent group capable of bonding to the ring structure of P1. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R''—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F. R' and R'' are independently of each other H, aryl or alkyl with 1 to 12 C-atoms. W and W' are H, halogen atoms, e.g., F, Cl, Br, and I, metallorganics, e.g., MgCl, MgBr, MgI, $Sn(R_2)_3$, where $R_2$ is $C_{1-6}$ alkyl or $C_{1-6}$ alkyl ether, boronic acid, boronic ester, vinyl units, e.g., —CH=CHR_3 where $R_3$ is H or $C_{1-6}$ alkyl, ether, i.e., —$OC_{1-6}$ alkyl, esters, i.e., —$COOC_{1-6}$ alkyl, —S—$COR_4$ and —$COR_4$ where $R_4$ is H or $C_{1-6}$ alkyl, —C≡CH, and polymerizable aromatic rings such as phenyl, naphthalene, pyrrole, and thiophene. Derivatives of the substituted claimed compositions can be formed prior to or after addition of the secondary or tertiary functionality.

Monomers suitable for producing homopolymers and copolymers are those where W and W' are H and represented by the formula M3, as follows:

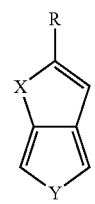

M3

X is S or Se, Y is S or Se, R are the groups described above with respect to formula M1.

Polymers, according to the present invention, include homopolymer having a repeating unit having formula P1, as follows:

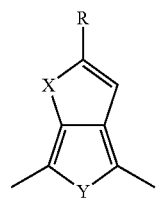

P1 where X is S or Se, Y is S or Se, wherein one or both of X and Y is Se, R is a substituent group. R may be any substituent group capable of bonding to the ring structure of P1. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R''—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F.

R' and R" are independently of each other H, aryl or alkyl with 1 to 12 C-atoms. The repeating structures according to the present invention may be substantially identical, forming a homopolymer, or may have R independently selected for each unit, resulting in a copolymeric compound. The repeating unit may be terminated in any suitable manner known in the art and may include functional or non-functional end groups.

In addition, the present invention includes branched or crosslinked oligomers, polymers and copolymers. For example, R as defined in P1 and M1 may include an alpha site, wherein the branching or crosslinking may take place. The following structure shows a branched polymeric material according to an embodiment of the present invention:

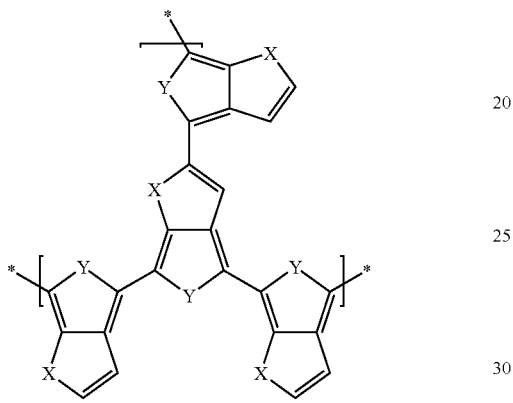

wherein X, Y and R are defined as above in formula P1. The present invention is not limited to the structure shown above and may include oligomeric and copolymeric structures including substitutent groups.

Electrically conducting oligomers and polymers comprised of copolymerized units of monomers are another aspect of the invention and may be represented by the formula P2, as follows:

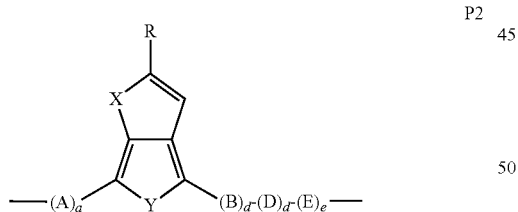

wherein X, Y and R are defined as above in formula P1. A, B, D, and E are independently of each other, and in case of multiple occurrence independently of one another, $-CZ^1=CZ^2-$, $-C\equiv C-$, or an arylene or heteroarylene group that is optionally substituted with one or more groups R. $Z^1$ and $Z^2$ are independently of each other H, F, Cl or CN. a, b, d, e are integers, including integers, independently of each other being 0, 1, 2 or 3.

The copolymer of formula P2 may terminate in any manner known in the art and may include any known polymerization end-groups.

Copolymeric structures, according to other embodiments of the present invention, include the following structures:

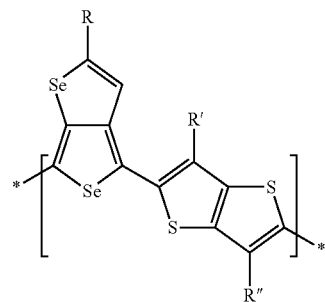
(C2)

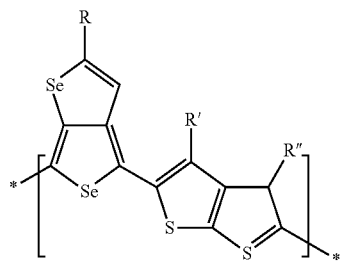
(C3)

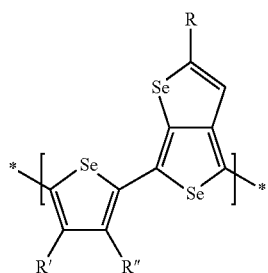
(C4)

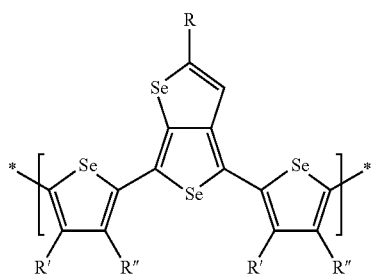
(C5)

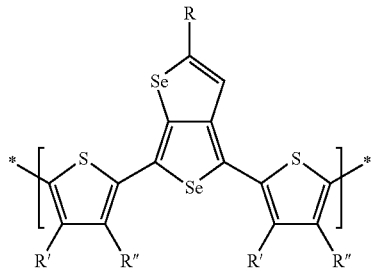
(C6)

(C7)
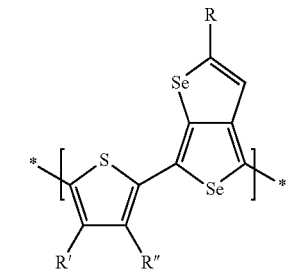
(C8)
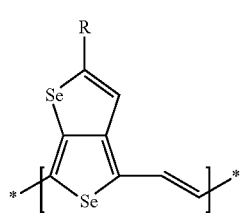
(C9)
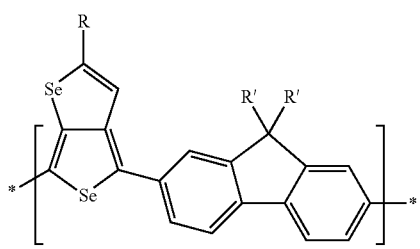
Additional copolymeric structures, according to other embodiments of the present invention, include the following structures:
(C10)
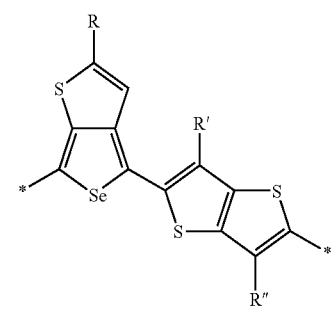
(C11)
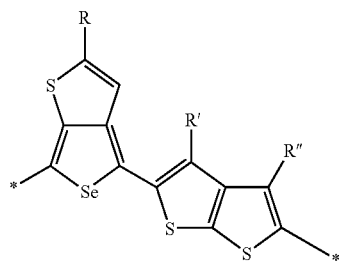
(C12)
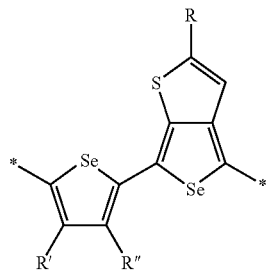
(C13)
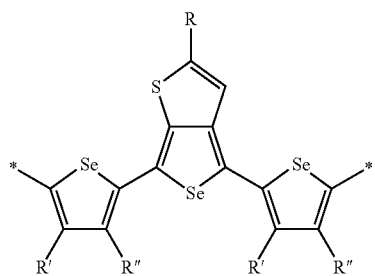
(C14)
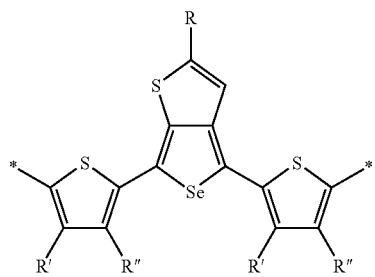
(C15)
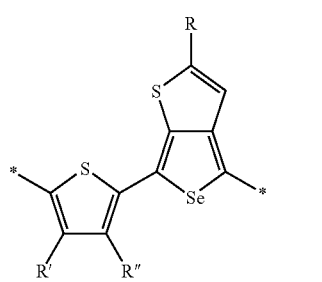
(C16)
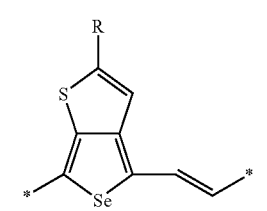
(C17)
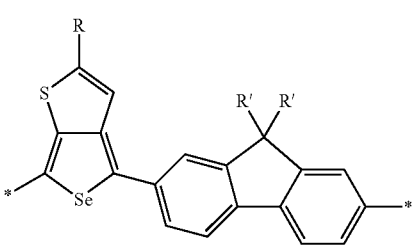
Still addition copolymeric structures, according to other embodiments of the present invention, include the following structures:

(C18) (C19) (C20) (C21) (C22)

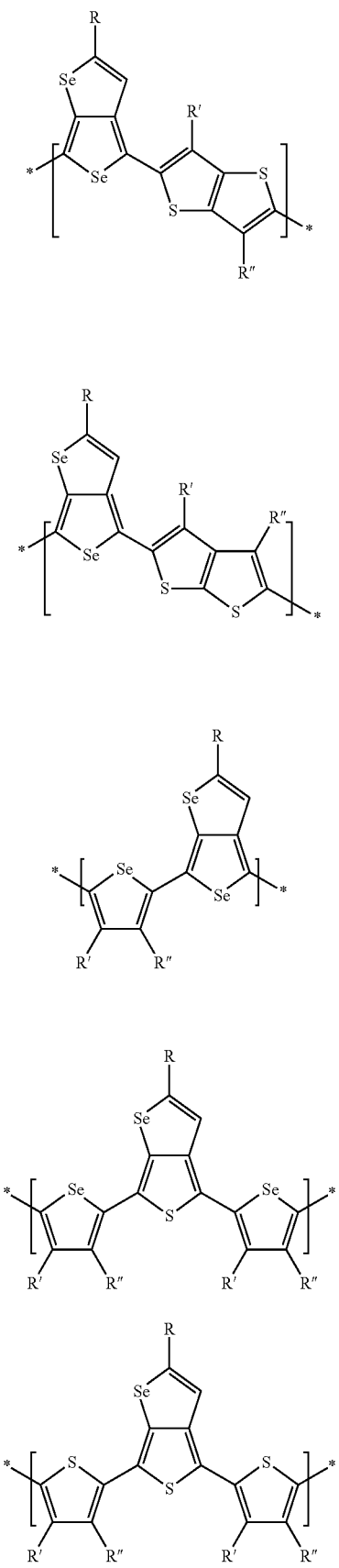

-continued (C23) (C24) (C25)

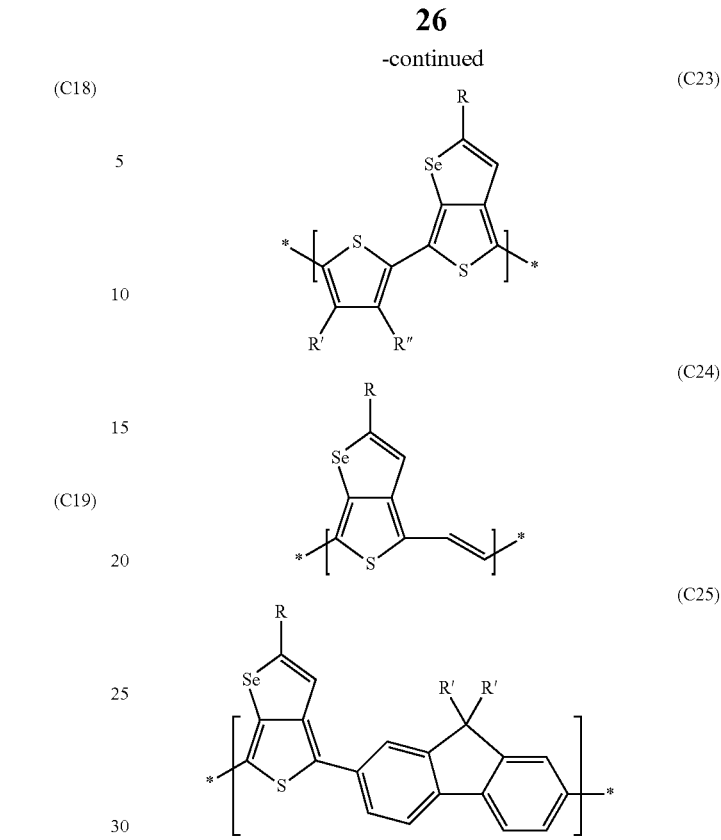

Polymerization of the monomeric or oligomeric compounds described above may take place through one of several reaction mechanisms. Possible reaction mechanisms include 1) aqueous phase/oxidant polymerization, 2) organic solvent phase/oxidant polymerization, 3) aqueous phase/organic phase/oxidant polymerization, 4) metal catalyst polymerization, 5) electrochemical polymerization and 6) solid state polymerization.

Typical reaction conditions for aqueous phase polymerization include temperatures ranging from 0° to about 100° C. The polymerization is continued for a period of time until the reaction is completed to affect the desired degree of polymerization. The degree of polymerization is not a critical element of this invention, but shall vary depending upon the end use application. The desired degree of polymerization shall depend upon the end use as is readily determined by one of ordinary skill in the art without undue experimentation. The polymerization time may range between a few minutes up to about 48 hours and depends on a number of factors including the size of the reactor utilized in the polymerization, the polymerization temperature and the oxidant utilized in the polymerization process.

The amount of polyanion and oxidant to be employed in the aqueous polymerization method may broadly vary and can be determined for any given polymerization without undue experimentation. For example the weight ratio of a selenolo[3,4-b]thiophene monomer to a desired polyanion typically ranges from 0.001 to 50, and in some cases 0.05 to 1.0. The molar ratio of selenolo[3,4-b]thiophene monomer to a desired oxidant typically ranges from 0.01 to 12 and in some cases 0.1 to 8.0. In another example, the weight ratio of a selenolo[2,3-c]thiophene monomer to a desired polyanion typically ranges from 0.001 to 50, and in some cases 0.05 to 1.0. The molar ratio of Selenolo[2,3-c]thiophene monomer to a desired oxidant typically ranges from 0.01 to 12 can in some cases 0.1 to 8.0.

The polyanions may include polymeric acids having sufficient acid strength to form colloids, including, but not limited to acid strengths of $pK_a$ of 6 or less. Suitable polyanions include an anion of a polyphosphonic acid and polyphosphoric acid, polycarboxylic acid, such as polyacrylic acid, polymethacrylic acid, polymaleic acid, and polymeric sulfonic acids, such as polystyrene sulfonic acid and polyvinyl sulfonic acid, mixed polyacids, such as polystyrenesulfonic acid-co-maleic acid, and colloid-forming polymeric acid, such as fluorinated sulfonic acid polymers and NAFION®. The polycarboxylic and polysulfonic acids may also be copolymers of vinyl carboxylic and vinyl sulfonic acids with other monomers, such as acrylates and styrene. The molecular weight of the acids supplying the polyanions can be in the range from 1,000 to 500,000, in some cases from 2000 to 500,000 and if desired about 70,000. The acids from which the polyanions are derived are commercially available or may be produced by known methods. Furthermore, the acid content usually expressed as equivalent weight (EW) may vary significantly to achieve the desired electronic properties.

One polyanion suitable for use in the present invention includes aqueous dispersions of fluorinated sulfonic acid polymers, such as fluorinated sulfonic acid polymers available commercially as Nafion® dispersions, from E. I. du Pont de Nemours and Company (Wilmington, Del.). An example of a suitable FSA polymer comprises a copolymer having a structure:

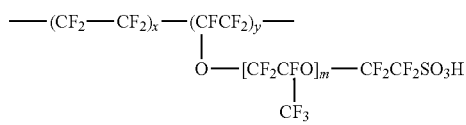

The copolymer comprises tetrafluoroethylene and perfluoro(4-methyl-3,6-dioxa-7-octene-1-sulfonic acid) wherein m=1.

Another embodiment of the present invention includes dispersions and solutions of aqueous and non-aqueous solvents, containing compositions according to the structure P1 and polymeric acid doped compositions of P1. Polymeric acid doped compositions are compositions that include the repeating unit P1 and have polymerized reaction products resulting from the reaction of the monomer or oligomer in the presence of polymeric acid, such as, but not limited to, a fluorinated sulfonic acid polymer or poly(styrene sulfonic acid). The polymer acid doped compositions may include sulfonic polymeric or oligomeric groups, reaction products or compounds bonded, covalently, ionically or otherwise, to the monomeric, oligomeric, polymeric or copolymeric structure according to P1. In one embodiment, the composition includes an aqueous dispersion of a polymeric acid doped polymer according to P1.

Oxidants suitable for use with the present invention include oxidants known to be suitable for oxidative polymerization of pyrrole. These oxidants are described, for example, in J. Am. Chem. Soc. 85, 484 (1963). Inexpensive oxidants which are easy to handle, such as iron (III) salts including, but not limited to, $Fe_2(SO_4)_3$, $FeCl_3$, $Fe(ClO_4)_3$ and the iron (III) salts of organic acids and inorganic acids containing organic residues, $H_2O_2$, $K_2Cr_2O_7$, alkali or ammonium persulfates, alkali perborates, potassium permanganate and copper salts such as copper tetrafluoroborate. In addition iodine, air and oxygen may advantageously be used as oxidants. Persulfates and the iron (III) salts of organic acids and inorganic acids containing organic residues are useful because they are not corrosive.

Examples which may be mentioned of iron (III) salts of organic acids are the Fe(III) salts of $C_{1-30}$ alkyl sulfonic acids, such as methane or dodecane sulfonic acid; aliphatic $C_{1-20}$ carboxylic acids, such as 2-ethylhexylcarboxylic acid, aliphatic perfluorocarboxylic acids, such as trifluoroacetic acid and perfluorooctanoic acid; aliphatic dicarboxylic acids, such as oxalic acid and, aromatic, optionally $C_{1-20}$-alkyl-substituted sulfonic acids, such as benzenesulfonic acid, p-toluenesulfonic acid and dodecyl benzenesulfonic acid and mixtures of the aforementioned Fe(III) salts of organic acids. Examples of iron (III) salts of inorganic acids containing organic residues are the iron (III) salts of sulfuric acid semiesters of $C_{1-20}$ alkanols, for example the Fe(III) salt of lauryl sulfate. It is also possible to employ mixtures of these above-mentioned Fe(III) salts of organic acids.

For the oxidative polymerization of the monomer according to an embodiment of the present invention, 2 to 2,5 equivalents of oxidant are theoretically required per mol of monomer (see e.g. J. Polym. Sc. Part A Polymer Chemistry Vol. 26, S, 1287 (1988)). In practice, however, the oxidant is applied in a certain excess, e.g. in an excess of 0.1 to 2 equivalents per mol of monomer.

The use of persulphates and iron (III) salts of organic acids and of inorganic acids containing organic radicals has the great application advantages that they do not have a corrosive action and, in particular, that the oxidation of the monomers of the formula M1 proceeds so slowly when they are used, monomers and oxidants can be applied together onto a metal foil in the form of a solution or from a printing paste. In this embodiment, after application of the solution or the paste, the oxidation can be accelerated by warming the coated metal foil.

When the other abovementioned oxidants such as $FeCl_3$, $H_2O_2$ or perborates are used, the oxidative polymerization proceeds so quickly that separate application of oxidants and monomer onto the substrate to be coated is necessary, but, in contrast, warming is no longer necessary.

Examples which may be mentioned of iron (III) salts of inorganic acids containing organic radicals are the iron (III) salts of the monoesters of sulphuric acid with $C_1$-$C_{20}$-alkanols, for example the Fe (III) salt of lauryl sulphate.

Polymers, including homopolymers may be formed by the following aqueous phase reaction:

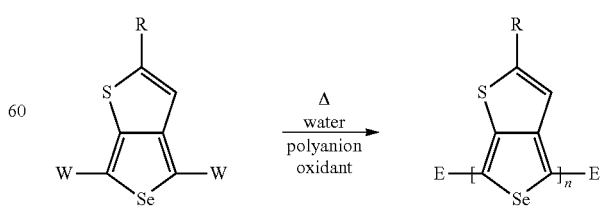

Copolymers according to the present invention may be formed by the following reaction:

Copolymers according to the present invention may be formed by the following reaction:

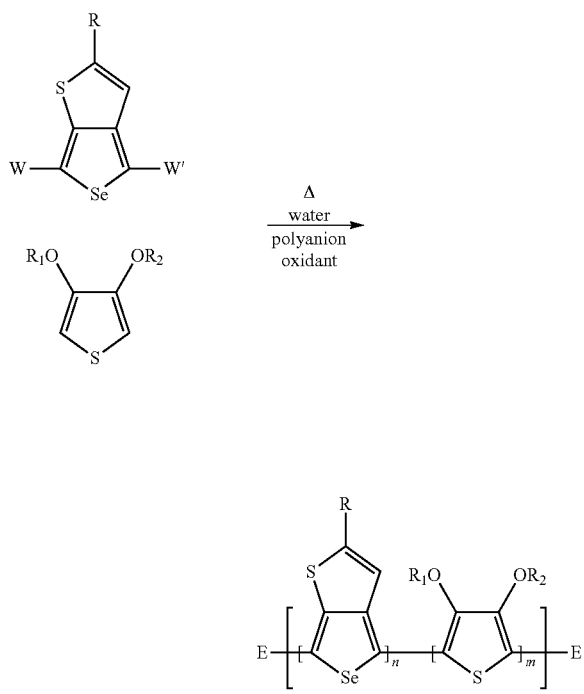

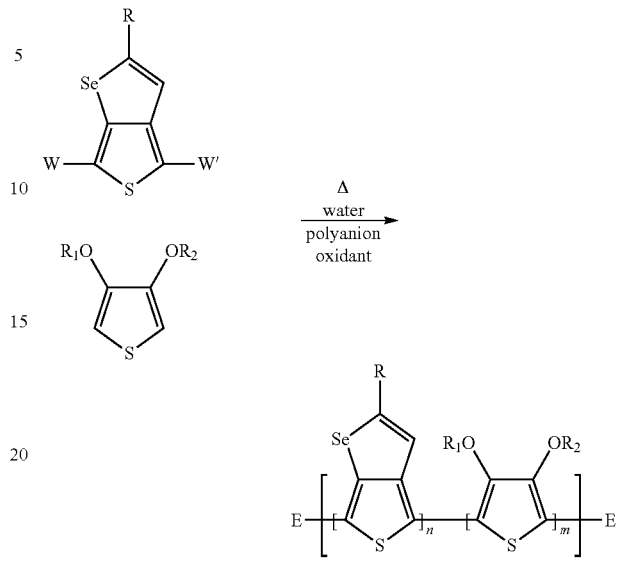

Although the above copolymerization reaction shows a substituted thiophene as the copolymerization agent, any number of compounds (i.e. any aryl, heteroaryl) may be used to polymerize in the reaction according to the present invention.

The oxidative polymerization of the monomers described above in the organic solvent phase is generally carried out at temperatures of from about 20° to about 250° C., in some cases at temperatures of from 20° and 200° C., depending on the oxidant used and the reaction time desired. Polymers, including homopolymers may be formed by the following organic phase reaction:

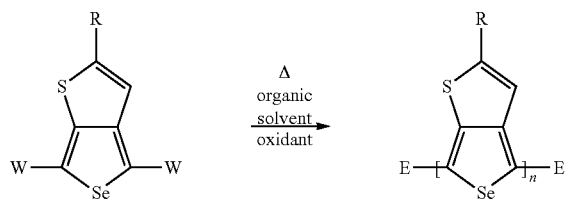

In another embodiment, polymers, including homopolymers may be formed by the following aqueous phase reaction:

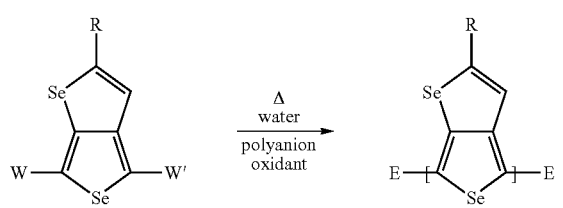

Copolymers according to the present invention may be formed by the following reaction:

Although the above copolymerization reaction shows a substituted thiophene as the copolymerization agent, any number of compounds (i.e. any aryl, heteroaryl) may be used to polymerize in the reaction according to the present invention.

The oxidative polymerization of the monomers described above in the organic solvent phase is generally carried out at temperatures of from about 20° to about 250° C., in some cases at temperatures of from 20° and 200° C., depending on the oxidant used and the reaction time desired. Polymers, including homopolymers may be formed by the following organic phase reaction:

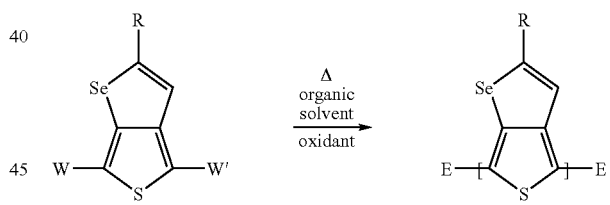

Like in the aqueous phase, copolymers may also be formed by providing additional monomer structures. Solvents suitable for use with the monomers of the formula M1 and/or oxidants are, in particular, the following organic solvents which are inert under the reaction conditions: aliphatic alcohols such as methanol, ethanol and i-propanol; aliphatic ketones such as acetone and methyl ethyl ketone; aliphatic carboxylic esters such as ethyl acetate and butyl acetate; aromatic hydrocarbons such as toluene and xylene; aliphatic hydrocarbons such as hexane, heptane and cyclohexane; chlorinated hydrocarbons such as dichloromethane and dichloroethane; aliphatic nitriles such as acetonitrile; aliphatic sulphoxides and sulphones such as dimethyl sulphoxide and sulpholane; aliphatic carboxamides such as methyl acetamide and dimethylformamide; aliphatic and araliphatic ethers such as diethyl ether and anisole. In addition, water or mixtures of water with the abovementioned organic solvents can also be used as solvents.

The oxidants suitable for use in the organic phase oxidation reaction include the same oxidant suitable for use in the aqueous phase oxidation reaction, discussed above.

When the monomers or oligomers and the oxidants are applied separately, substrates can be initially coated with the solution of the oxidant and subsequently with the solution of the monomer. When, as suitable, the monomer and oxidant are applied together onto substrate, the substrate is only coated with one solution, namely a solution containing a monomer and an oxidant. Since a portion of the monomer evaporates during this joint application the oxidant is added to the solution in this method of procedure in an amount, which is reduced in accordance with the anticipated loss of monomer.

In addition, the above solutions may contain organic binders which are soluble in organic solvents, such as poly(vinyl acetate), polycarbonate, poly(vinyl butyrate), polyacrylates, polymethacrylates, polystyrene, polyacrylonitrile, poly(vinyl chloride), polybutadiene, polyisoprene, polyethers, polyesters, silicones, and pyrrole/acrylate, vinyl acetate/acrylate and ethylene/vinyl acetate copolymers each of which are soluble in organic solvents. It is also possible to use water-soluble binders such as polyvinyl alcohols as thickeners.

The nature of the polymerization and the desired polymer may be controlled depending upon what W and W' groups are present. Carbon-carbon bond forming reactions may be completed following known methods. Known methods suitable for use with the monomer of the present invention include, but are not limited to the Suzuki Reaction, the Yamamoto Reaction, the Heck Reaction, the Stille Reaction, the Sonogashira-Hagihara Reaction, the Kumada-Corriu Reaction, the Riecke Reaction, and the McCullogh Reaction.

Monomers of the Formula M1 lend themselves to metal-catalyzed polymerizations as described in the open literature. For examples see, Heck, Chem. Rev. 2000, 100, 3009-3066; Stille, Chem. Rev. 2003, 103, 169-196; Suzuki, Chem. Rev. 1995, 95, 2457-2483; Sonogashira-Hagihara, Chem. Rev. 2003, 103, 1979-2017; and Kumada-Corriu, Chem. Rev. 2002, 102, 1359-1469 incorporated herein by reference. Conditions can vary greatly depending on the nature the W and W' substituents.

An alternate method for preparing oligomers and polymers, such as poly(selenolo[2,3-c]thiophene), involves an electrochemical process wherein selenolo[2,3-c]thiophene is polymerized in an electrochemical cell using a three electrode configuration. A suitable three electrode configuration comprises a button working electrode selected from the group consisting of platinum, gold and vitreous carbon button working electrodes, a platinum flag counter electrode and an Ag/Ag+ non-aqueous reference electrode. Suitable electrolytes are selected from the group consisting of tetrabutylammonium perchlorate/acetonitrile, lithium triflate/acetonitrile and tetrabutylammonium hexafluorophosphate/acetonitrile.

Polymers, including homopolymers may be formed by the following electrochemical reaction:

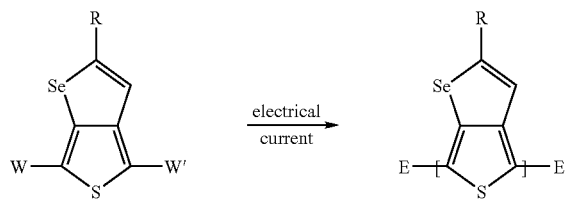

Selenolo[2,3-c]thiophene may undergo electrochemical oxidation at a peak above 1.1V to provide the polymer, poly(selenolo[2,3-c]thiophene) on the surface of the working electrode.

Conventional electrolytic cells can be utilized to practice the electrochemical process for making the compositions of matter of the present invention. The working electrode for making the compositions of matter of this invention can comprise platinum electrode and an effective electrolyte comprises hexafluorophosphate.

Polymerization is evident as indicated by the increase in current response for the lower redox process which corresponds to the reduction and oxidation of the conducting polymer that had been electroprecipitated onto the electrode surface.

The oxidative polymerization of selenolo[2,3-c]thiophene may be carried out in aqueous solution utilizing poly(styrene sulfonic acid) or NAFION® as the polyanion and ammoniumpersulfate and/or iron (III) sulfate as the chemical oxidant.

The above described polymerization has been in terms of a homopolymerization but it is also possible to conduct a copolymerization of the selenolo[2,3-c]thiophene with another monomer such as 3,4-ethylenedioxythiophene or pyrrole.

EXAMPLES

The following illustrative examples are provided to further describe how to make and use the compositions of matter and are not intended to limit the scope of the claimed invention. Unless otherwise stated, parts and percentages in the examples are given by weight.

Example 1

Aqueous Synthesis of Poly(selenolo[2,3-c]thiophene)

50 mg of selenolo[2,3-c]thiophene and 830 mg of 18% poly(styrenesulfonic acid) water solution in 10 ml of deionized water was added to a 25 ml 1-neck flask. The mixture was stirred at 600 rpm. 113.0 mg (0.48 mmol) of $(NH_4)_2S_2O_8$ and 2 mg of $Fe_2(SO_4)_3$ were added to the reaction flask. The oxidative polymerization was carried out in excess of one hour. After polymerization, the aqueous solution was purified by ion exchange columns (Amberlite IR-120 and MP62) resulting in a deep black aqueous poly(selenolo[2,3-c]thiophene)/poly(styrene sulfonic acid) dispersion. Transparent films were prepared by spin coating the poly(selenolo[2,3-c]thiophene)/poly(styrene sulfonic acid) mixture onto glass substrates at 1,000 rpm yielding an electrically conductive surface.

Example 2

Aqueous Synthesis of Poly(selenolo[2,3-c]thiophene)

50 mg of selenolo[2,3-c]thiophene and 5.55 g of 18% poly(styrenesulfonic acid) water solution in 45 ml of deionized water was added to a 100 ml 1-neck flask. The mixture was stirred at 1200 rpm. 300 mg (1.98 mmol) of $Fe_2(SO_4)_3$ dissolved in 7 mL deionized water were added to the reaction flask. The oxidative polymerization was carried out in excess of one hour. After polymerization, the aqueous solution was purified by ion exchange columns, resulting in a deep black aqueous poly(1H-thieno[3,4-d]imidazol-2(3H)-one)/poly(styrene sulfonic acid) dispersion. Transparent films were prepared by spin coating the poly(selenolo[2,3-c]thiophene)/poly(styrene sulfonic acid) mixture onto glass substrates at 1,000 rpm yielding an electrically conductive surface.

Example 3

Aqueous Synthesis of Poly(selenolo[2,3-c]thiophene)

50 mg of 1 selenolo[2,3-c]thiophene and 8.4 g of 12% NAFION® perfluorinated ion-exchange resin water dispersion in 42 ml of deionized water was added to a 100 ml 1-neck flask. The mixture was stirred at 1200 rpm. 300 mg (1.98 mmol) of $Fe_2(SO_4)_3$ dissolved in 7 mL deionized water were added to the reaction flask. The oxidative polymerization was carried out in excess of one hour. After polymerization, the aqueous solution was purified by ion exchange columns, resulting in a deep black aqueous poly(selenolo[2,3-c]thiophene)/NAFION® dispersion displaying a pH of about 2.0. Transparent films were prepared by spin coating the poly(selenolo[2,3-c]thiophene)/NAFION® mixture onto glass substrates at 1,000 rpm yielding an electrically conductive surface.

Example 4

Aqueous Synthesis of Poly(selenolo[2,3-c]thiophene)

50 mg of selenolo[2,3-c]thiophene and 8.4 g of 12% NAFION® perfluorinated ion-exchange resin water dispersion in 42 ml of deionized water was added to a 100 ml 1-neck flask. The mixture was stirred at 1200 rpm. 113.0 mg (0.48 mmol) of $(NH_4)_2S_2O_8$ and 2 mg of $Fe_2(SO_4)_3$ were added to the reaction flask. The oxidative polymerization was carried out in excess of one hour. After polymerization, the aqueous solution was purified by ion exchange columns (Amberlite IR-120 and MP62) resulting in a deep black aqueous poly(selenolo[2,3-c]thiophene)/NAFION®dispersion. Transparent films were prepared by spin coating the poly(selenolo[2,3-c]thiophene)/NAFION® mixture onto glass substrates at 1,000 rpm yielding an electrically conductive surface.

Example 5

Solvent (in-Situ) Synthesis of Poly(selenolo[2,3-c]thiophene)

280 mg of selenolo[2,3-c]thiophene were dissolved in 15 mL anhydrous n-butanol. 2.25 g (3.3 mmol) of iron (III) p-toluenesulfonate hexahydrate dissolved in 5 mL of anhydrous n-butanol was added to the monomer solution resulting in a deep red solution. The mixture was drop cast on glass substrates and allowed to dry. The dried film was cured at temperatures up to 120° C. for up to 15 minutes. The resulting film was conductive as determined by the four-point-probe measurement. The formed polymer film appeared grey to the naked eye absorbing weakly and uniformly across the visible spectrum.

Example 6

Electrochemical Synthesis and Characterization of Poly(selenolo[2,3-c]thiophene)

Selenolo[2,3-c]thiophene was dissolved in tetrabutylammonium hexafluorophosphate/acetonitrile solution to a concentration of 5 mM monomer and 100 mM electrolyte and was electrochemically polymerized employing a 3-electrode configuration, using a platinum button working electrode (2 mm diameter), platinum flag counter electrode (1 cm²), and a Ag/Ag+ nonaqueous reference electrode (4.82 V versus vacuum level as determined by calibration with a ferrocene solution). The monomer exhibits a low oxidation potential with an onset at 5.6 eV. Polymerization was apparent from the current response increase in regular intervals at a lower redox potential upon repetitive scans.

The polymers electronic properties were evaluated in an acetonitrile solution being 100 mM in tetrabutylammonium hexafluorophosphate. Scan rate dependency was carried out at scan rates of 25, 50, 100, 200 and 400 mV/s. The peak current for the reductive process of the polymer was found to scale linearly with the scan rate indicating that poly(selenolo[2,3-c]thiophene) was adhered to the surface of the electrode. The formed polymer was evaluated by cyclic voltammetry and displayed an HOMO of −4.1 eV. The optical band gap was found to be 0.9 eV. Differential Pulse Voltammetry gave rise to a HOMO of −4.15 eV.

Example 7

PLED Device 3 patterned ITO substrates with surface resistance of 10-15 ohm/square were cleaned by ultrasonication sequentially in de-ionized water with detergent, de-ionized water, methanol, isopropanol, and acetone; each for 5 to 10 min. The ITO substrate was allowed to dry between different cleaning solvents. (The substrate used in this examples refers in FIG. 1 to layer 1 and 2. Layer 1 being glass and layer 2 being ITO) Then the ITO substrate was treated with oxygen plasma in an SPI Prep II plasma etcher for about 10 min. After that, the ITO substrate was spin coated with the dispersion derived from Example 3 at 1500 rpm for 1 min on a Laurell Model WS-400-N6PP spinner. (The dispersion refers in FIG. 1 to layer 4, and if desired, in order to improve performance, one or more interlayer materials designated in FIG. 1 as layer 3 may be deposited before layer 4 is being deposited.) ITO substrates were then annealed at 180° C. for 15 min. After the annealing, a layer of about 80-nm-thick LUMATION Green 1304 (supplied by Sumitomo Chemical Company) was spin coated from toluene solution (The LUMATION Green 1304 corresponds to layer 6 in FIG. 1. This layer has been directly deposited onto layer 4 in this example. However, if desired, one or more interlayers may be deposited between layer 4 and 6 to attain tailored performances). The samples were then baked at 130° C. for 20 min on a hotplate under $N_2$ protection. The samples were then transferred into the chamber of a vacuum evaporator, which was located inside an argon atmosphere glove box. A layer of 5 nm thick Ba was vacuum deposited at below $1 \times 10^{-7}$ Torr through a mask at a rate of ~1.5 Å/s, and another layer of 120 nm thick Ag was vacuum deposited on top of the Ba layer at a deposition rate of ~3.0-4.0 Å/s (This layer corresponds to layer 8 in FIG. 1). The devices were then encapsulated with glass cover lid and UV curable epoxy in the argon glove box. The devices were taken out of the glove box and then measured for IV curves and brightness. The devices exhibited an efficiency of 12.5 cd/A at 5000 cd/m², of 12.6 cd/A at 2500 cd/m², and of 12.3 cd/A at 1000 cd/m². After the characterization, the devices were then put on a CDT Eclipse PLED Lifetime Tester for DC lifetime test at an initial brightness of 5000 cd/m². The device half life is defined as the time it takes for the brightness of the device to reach 50% of the initial value of 5000 cd/m², i.e. 25000 cd/m². The device half life was 660 hr.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A composition of matter comprising:
a semiconducting copolymer doped with a polymeric acid of sufficient strength to form colloids, the copolymer containing a repeating unit having formula:

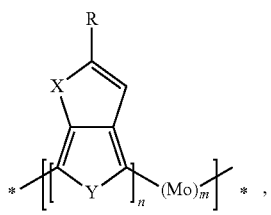

wherein X is Se, Y is S, R is a substituent group, n and m are independently selected integers having a total n+m of greater than or equal to 2, and Mo includes thieno[3,4-b]thiophene, thieno[3,2-b]thiophene, substituted thieno[3,4-b]thiophenes, substituted thieno[3,2-b]thiophene, dithieno[3,4-b:3',4'-d]thiophene, bithiophene, phenylene, substituted phenylenes, naphthalene, substituted naphthalenes, biphenyl, terphenyl, or substituted terphenyl; and
a solvent or water.

2. The composition of claim 1, wherein the compositions is an aqueous dispersion.

3. The composition of claim 1, wherein the composition is a solution.

4. The composition of claim 1, wherein the composition comprises an organic solvent and water.

5. The composition of claim 1, wherein the polymeric acid is poly(styrene sulfonic acid).

6. The composition of claim 1, wherein the polymeric acid is fluorinated sulfonic acid polymer.

7. The composition of claim 1, wherein R is selected from the group consisting of hydrogen, isotopes of hydrogen, hydroxyl, alkyl, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, and alkyl and phenyl substituted with one or more sulfonic acid, sulfonic acid derivative, phosphoric acid, phosphoric acid derivative, carboxylic acid, carboxylic acid derivative, halo, amino, nitro, hydroxyl, cyano, and epoxy moieties.

8. The composition of claim 7 wherein R is H.

9. The composition of claim 1, wherein Mo is selected from the group consisting of selenolo[3,4-b]thiophenes, selenolo[2,3-c]thiophenes and selenolo[2,3-c]selenophenes.

10. The composition of claim 1, wherein Mo is selected from the group consisting of the following the compound formulas:

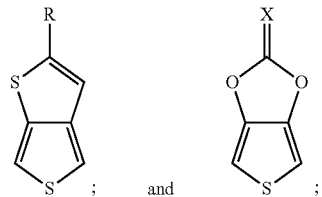

wherein X denotes S, O, Se, or NH; and

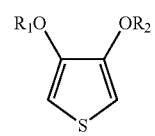

wherein $R_1$ and $R_2$ are independently selected from the group consisting of H, C1-C4 alkyl groups, 1,2 cyclohexylene radical, phenyl substituted phenyl and combinations thereof.

11. The composition of claim 1, wherein the composition includes an additive selected from the group consisting of particulate copper, silver, nickel, aluminum, carbon black, talc, mica, wollastonite, silica, clay, $TiO_2$, dyes, pigments, and combinations thereof.

12. A composition, comprising:
a semiconducting copolymer doped with a polymeric acid of sufficient strength to form colloids, the copolymer comprising the following repeating unit:

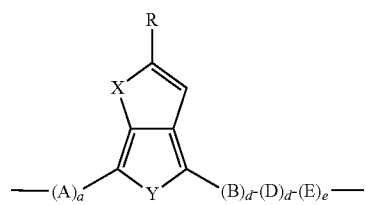

wherein X is Se, Y is S, R is a substituent group, each of a and b, independently, is 1, 2, or 3, each of d and e, independently, is 0, 1, 2, or 3, A, B, D, and E are independently selected from the group consisting of $-CZ^1=CZ^2-$, $-C\equiv C-$, arylene, heteroarylene, substituted $-CZ^1=CZ^2-$, substituted $-C\equiv C-$, substituted arylene, and substituted heteroarylene, the substituted $-CZ^1=CZ^2-$, substituted $-C\equiv C-$, substituted arylene, and substituted heteroarylene, independently being substituted with R, and the $Z^1$ and $Z^2$ being independently selected from the group consisting of H, F, Cl and CN.

13. A composition, comprising:
a semiconducting copolymer doped with a polymeric acid of sufficient strength to form colloids, the copolymer comprising a repeating unit selected from the group consisting of:

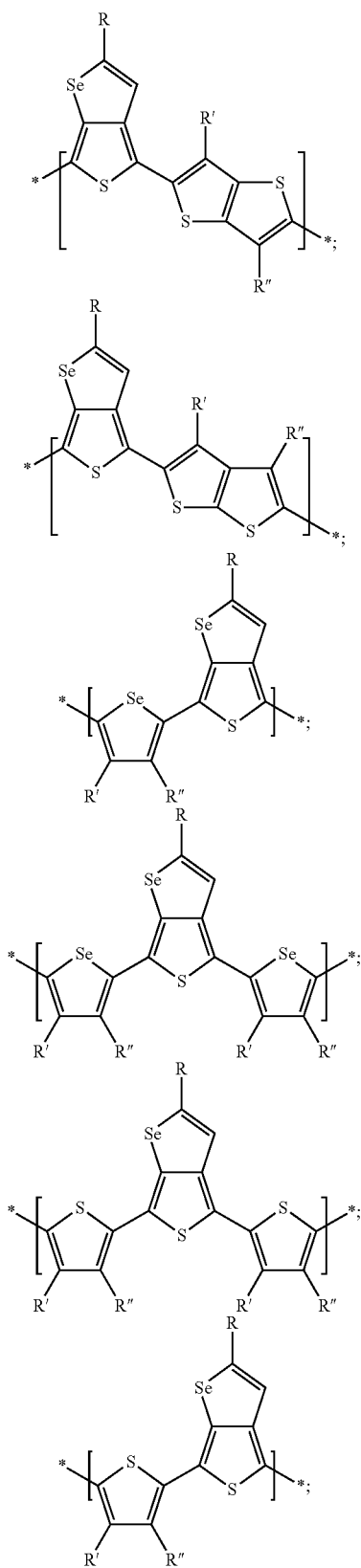

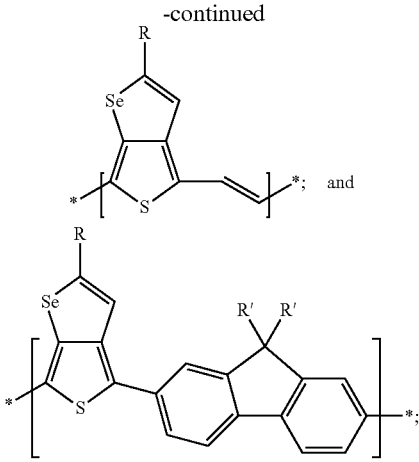

wherein R is selected from the group consisting of hydrogen, isotopes of hydrogen, hydroxyl, alkyl, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkyl amino, dialkylamino, arylarylamino, arylthio, heteroaryl, arylsulfinyl, alkoxycarbonyl, aryl sulfonyl, carboxyl, halogen, nitro, cyano, sulfonic acid, and alkyl and phenyl substituted with one or more sulfonic acid, sulfonic acid derivative, phosphoric acid, phosphoric acid derivative, carboxylic acid, carboxylic acid derivative, halo, amino, nitro, hydroxyl, cyano, and epoxy moieties, wherein R' and R" are independently of each other H, aryl or alkyl with 1 to 12 C-atoms.

14. A composition, comprising:

a semiconducting copolymer doped with a polymeric acid of sufficient strength to form colloids, the copolymer comprising the following repeat unit:

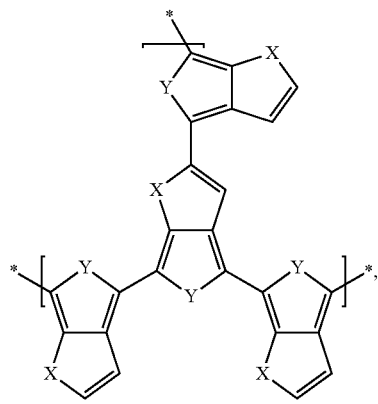

wherein X is Se and Y is S.

* * * * *